(12) United States Patent
Krasilchikov et al.

(10) Patent No.: US 7,383,740 B2
(45) Date of Patent: Jun. 10, 2008

(54) SPIROMETER

(75) Inventors: Yehezkel Krasilchikov, Katzrin (IL); Anna Litvak, Bene Ayesh (IL); Felix Shestatski, Carmiel (IL)

(73) Assignee: Spirojet Medical Ltd, Katzrin (IL)

( * ) Notice: Subject to any disclaimer, the term of this patent is extended or adjusted under 35 U.S.C. 154(b) by 0 days.

(21) Appl. No.: 10/579,546

(22) PCT Filed: Nov. 17, 2004

(86) PCT No.: PCT/IL2004/001057

§ 371 (c)(1),
(2), (4) Date: Mar. 13, 2007

(87) PCT Pub. No.: WO2005/046426

PCT Pub. Date: May 26, 2005

(65) Prior Publication Data

US 2007/0239058 A1 Oct. 11, 2007

(51) Int. Cl.
*G01F 1/20* (2006.01)

(52) U.S. Cl. .................................. 73/861.19

(58) Field of Classification Search ........ 600/538–542; 73/861.19, 861.21, 861.23
See application file for complete search history.

(56) References Cited

U.S. PATENT DOCUMENTS

| 3,714,828 | A | 2/1973 | Durkan |
| 3,797,479 | A | 3/1974 | Graham |
| 4,182,172 | A | 1/1980 | Wennberg et al. |
| 4,930,357 | A | 6/1990 | Thurston et al. |
| 5,137,026 | A | 8/1992 | Waterson et al. |
| 5,864,067 | A * | 1/1999 | Ligneul et al. .......... 73/861.21 |
| 6,216,702 | B1 * | 4/2001 | Gjersøe ...................... 128/898 |
| 6,477,900 | B2 | 11/2002 | Krasilchikov et al. |
| 7,094,208 | B2 * | 8/2006 | Williams et al. ............ 600/538 |
| 2003/0191407 | A1 | 10/2003 | Williams et al. |

FOREIGN PATENT DOCUMENTS

IL    135902    6/2005

* cited by examiner

*Primary Examiner*—Jewel Thompson
(74) *Attorney, Agent, or Firm*—The Nath Law Group; Jerald Meyer; Derek Richmond

(57) ABSTRACT

Pocket-size medical spirometer comprising a housing and a measurement unit (MU), for measuring rate of total flow when a user exhales through the spirometer. The MU comprises a fluidic jet oscillator adapted to generate oscillating flow with frequency dependent on the rate of flow therethrough. The MU is disposed within the housing so as to form a bypass flow path defined between an outer surface of the MU and an inner surface of the housing. A measurement flow path is defined through the fluidic jet oscillator, such that the total flow is divided into a bypass flow and a measurement flow, the latter being less than the former at least by an order of magnitude. The spirometer further comprises a pressure or velocity transducer and an electronic circuit adapted to derive the total flow rate or volume from the transducer signal.

47 Claims, 6 Drawing Sheets

SPIROMETER

FIELD OF THE INVENTION

This invention relates to medical spirometers, in particular to spirometers using fluidic elements for measurement

BACKGROUND OF THE INVENTION

Medical spirometers are used for testing/measuring respiratory functions of humans, including instant flow rate during respiration (peak-flow meters) and total volume discharge or vital capacity. Fluidic elements, such as fluidic oscillators are known for their stability, linear characteristics and reliability, and are used in such spirometers.

U.S. Pat. No. 3,714,828 describes a device for measuring the pulmonary function of a patient, comprising a fluid oscillator and a digital counter. In one embodiment, a sample of the flow is diverted by a Pitot tube to the fluid oscillator. The device is designed for measuring expiratory gases from a hospital patient who has been given a volatile anesthetic.

U.S. Pat. No. 4,182,172 discloses a flow meter of fluidic oscillator type designed for measuring the ventilation of a moving human being or an animal. The flow meter is small, light and portable. The pressure drop is described as minimal but the whole flow passes through the oscillator. The flow oscillations are detected by a suitably disposed ultrasonic transmitter and receiver.

U.S. Pat. No. 4,930,357 describes a volumetric flow meter comprising a fluidic oscillator and a plurality of parallel fluid flow bypass channels. Each channel has a special flow restriction to obtain pressure drop equal to the one across the oscillator for easier calculation of the total flow. The oscillating pressure in the feedback channels of the oscillator is measured by two sensing chambers connected to the feedback channels and closed by diaphragms with transducers thereon. The other side of the diaphragms is exposed to the atmosphere.

SUMMARY OF THE INVENTION

In accordance with one aspect of the present invention, there is provided a medical spirometer comprising a housing with a flow inlet and a flow outlet and a measurement unit (MU) for measuring rate of total flow between the inlet and the outlet when a user exhales through the spirometer. The MU comprises one fluidic jet oscillator adapted to generate oscillating flow characterized by an oscillating parameter with frequency dependent on rate of flow through said jet oscillator, and a transducer adapted to convert said oscillating parameter into an oscillating electric signal. The fluidic oscillator may be implemented as a sandwich of two or more parallel jet oscillators for obtaining stable oscillations.

The MU is disposed within the housing so as to form a bypass flow path defined between an outer surface of the MU and an inner surface of the housing. A measurement flow path is defined through the fluidic jet oscillator such that the total flow is divided into a bypass flow and a measurement flow.

The measurement flow rate may be less than the bypass flow rate at least by an order of magnitude. Preferably, the bypass flow path is free of obstructions increasing its pressure drop.

The spirometer may be a pocket-size stand-alone device or a miniature instrument used in mobile or stationary measurement circuits.

The MU further comprises an electronic circuit (processor) adapted to measure the frequency of the oscillating signal and to derive the total flow rate therefrom. Preferably, the electronic circuit is adapted to store coefficients obtained in previous calibration of the spirometer and to use them for deriving the total flow rate. Preferably, the electronic circuit is adapted to measure the frequency by counting pulses of the oscillating parameter.

The electronic circuit may be further adapted to integrate the total flow rate, thereby measuring the total flow volume per predetermined time.

The oscillating parameter may be the flow velocity which can be measured by a hot wire. Alternatively, the oscillating parameter may be the flow pressure which can be measured by a pressure transducer.

Preferably, the pressure transducer is of differential type, for example with a chamber divided by a flexible membrane and a piezoelectric element mounted on the membrane. The jet oscillator has two feed-back channels, each with a pressure port, and one of the pressure ports is connected to one side of the membrane, while the other of the pressure ports is connected to the other side of the membrane. Thus the registration of each pulse is facilitated as the pressures in the feed-back channels oscillate in opposing phases.

The spirometer may comprise valve means such that a measurement flow through the jet oscillator is created also when the user inhales through the spirometer, thereby enabling measuring of total flow rate at inhale. Alternatively, the jet oscillator or the MU can be made movable to assume a second position with respect to the housing, such that a measurement flow through the jet oscillator would be created when the user inhales.

The MU may comprise a second fluidic jet oscillator similar and parallel to the first one but oppositely orientated and defining a second measurement flow path within the MU, such that a second measurement flow is created when the user inhales through the spirometer. The spirometer further may comprise valve means such that the first measurement flow path is open only when the user exhales while the second measurement flow path is open only when the user inhales. The valve means may include one check valve associated with the first measurement flow path and one check valve associated with the second measurement flow path.

The second jet oscillator may be connected to the same pressure transducer as the first jet oscillator, so that the MU may have no other pressure transducers.

Alternatively, the spirometer may comprise a second transducer adapted to convert an oscillating flow parameter of the second jet oscillator into a second oscillating electric signal. In a variation of this embodiment, the first and second measurement flow paths have no valve means and are open both when the user inhales and exhales, such that at exhaling the first jet oscillator works in straight flow while the second jet oscillator works in reverse flow and vice-versa. The electronic processor is adapted to recognize whether the user inhales or exhales by different patterns of the respective first and the second oscillating signals.

The signal patterns may differ in that at exhaling the first (straight) oscillating signal has regular pulse structure while the second (reverse) oscillating signal is irregular (hereinafter 'noise'). The front edge of the recognizable first pulse in the first oscillating signal comes before the noise is recognized, which is used by the processor for the distinction between the signals. Correspondingly, at inhaling the second oscillating signal has regular pulse structure while said first oscillating signal is noise, the front edge of the first pulse in the second oscillating signal coming before the noise.

The spirometer further may comprise a means to display flow measurement results to the user.

The spirometer may comprise means for storing measurement data and communicating the data to an external device, preferably bi-directionally.

The communication means may include interface to a cellular phone enabling transmission of the data through the cellular phone network. The spirometer housing may be designed for mounting to the housing of the cellular phone. The spirometer may further include program means transferable to or resident in the cellular phone allowing to display flow measurement results on the display of the cellular phone. Alternatively, the spirometer may include a built-in cellular phone enabling transmission of the data through a cellular phone network.

The spirometer may further comprise means for identifying a medical condition using the flow measurement results, and for warning the user. The spirometer further comprises input means for entering personal data of the user, which data may be used for identifying the medical condition. The spirometer may also comprise means for suggesting preventive measures to the user upon identifying the medical condition.

The spirometer may be designed to have a housing adapted to accommodate a dispenser with medicine for inhaling. The housing preferably has a channel for delivery of the medicine to the user's mouth, connecting an outlet of the dispenser to the flow inlet.

The bypass channel may be formed as an annular channel with the delivery channel opening within the bypass channel, for forming a jet of dispersed medicine in the core of the airflow.

The spirometer may further comprise a second fluidic jet oscillator defining a second flow path such that a second oscillating flow is created when the user inhales through the spirometer. The medicine delivery channel may then connect the outlet of the dispenser to the inlet of the second jet oscillator, such that the medicine passes through the second flow path for enhanced mixing. A surrounding bypass channel may be formed in the body of the second fluidic jet oscillator.

According to another aspect of the present invention, there are provided inhaler-dispenser devices with improved aerodynamic features.

One example of such inhaler-dispenser comprises a housing adapted to accommodate a dispenser with medicine for inhaling. The housing further has an inhaling passage with inlet air opening and outlet mouthpiece such that upon inhaling, airflow runs from the inlet to the outlet, this housing further having a delivery channel for delivery of the medicine into the airflow. An outlet end of the delivery channel is disposed such that, at inhale, a dose of said medicine is delivered to a central core of the airflow.

The inhaling passage may include a fluidic jet oscillator with an inlet connected to the inlet opening and an outlet connected to the mouthpiece, the delivery channel opening into the inlet of the fluidic jet oscillator, for enhanced mixing of the medicine. An annular bypass channel may be formed in the body of the fluidic jet oscillator such that, upon inhaling, the outlet jet flow of the fluidic jet oscillator carrying said medicine is surrounded by a parallel flow through the bypass channel.

According to a still further aspect of the present invention, there is provided a method for measurement of a user's inhale and exhale rate of flow by means of two fluidic jet oscillators, each having an inlet and an outlet defining 'straight' flow direction used for measurement, and defining an inoperative 'reverse' flow, and adapted to generate oscillating flow characterized by an oscillating parameter dependent on rate of straight flow through the jet oscillator, with two respective transducers used to convert the oscillating parameters into oscillating electric signals having different signal patterns for 'straight' and 'reverse' flows. The method comprises:

arranging the fluidic jet oscillators in parallel and opposite flow directions such that, when the user exhales, the first jet oscillator works in the straight flow, and when the user inhales, the second jet oscillator works in the straight flow;

providing exhaling or inhaling flow through the fluidic jet oscillators;

obtaining oscillating electric signals from said transducers;

processing said signals to identify which of the two signals is associated with the 'straight' flow, using the pattern difference between the 'straight' flow and the 'reverse' flow signals from which transducer this signal is coming; and determining the flow rate from the identified signal.

The pattern difference may be in that the 'reverse' oscillating signal is noise while the 'straight' oscillating signal has regular pulse structure with the front edge of the first pulse coming before the noise.

The spirometer of the present invention may have miniature size, minimum pressure drop (no obstructions to breathing during measurement), precise and simple digital measurement (count of pulses), temperature independence, cheap production, convenient usage, disinfection and practically no maintenance. The spirometer may be handy, easy to carry around, for example as a key-holder, yet robust and reliable. It can be integrated with other pocket-size objects like mobile phones or medicine dispensers.

BRIEF DESCRIPTION OF THE DRAWINGS

In order to understand the invention and to see how it may be carried out in practice, different embodiments will now be described, by way of non-limiting examples only, with reference to the accompanying drawings, in which.

DETAILED DESCRIPTION OF THE INVENTION

Figure 1:
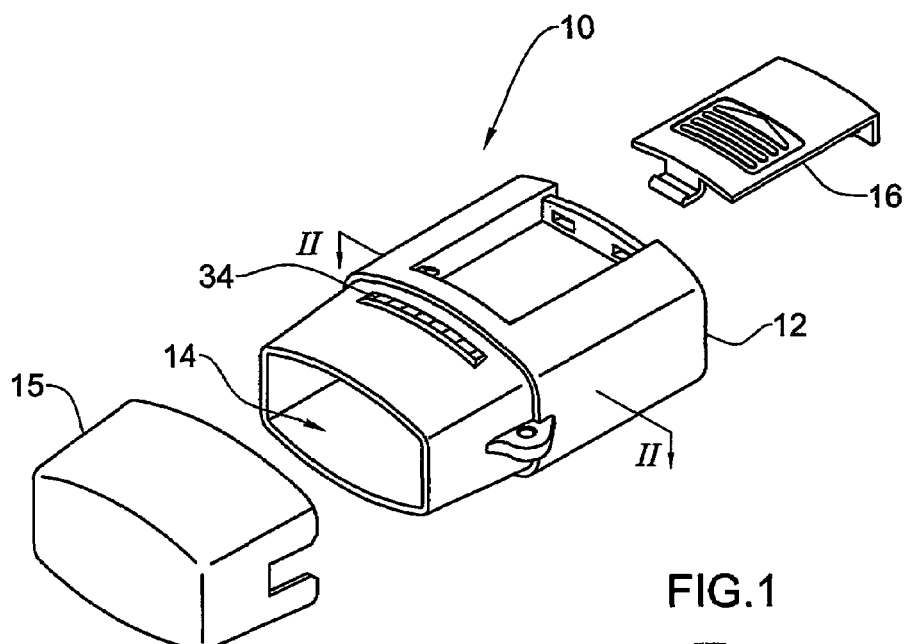
FIG. 1 is an exploded view of an example of a spirometer in accordance with one aspect of the present invention.
Figure 2:
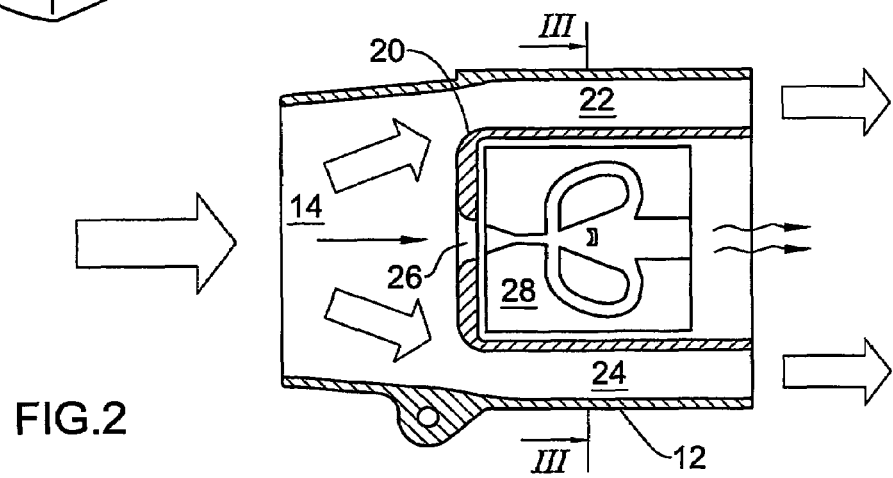
FIG. 2 is a longitudinal sectional view of the spirometer in FIG. 1.
Figure 3:
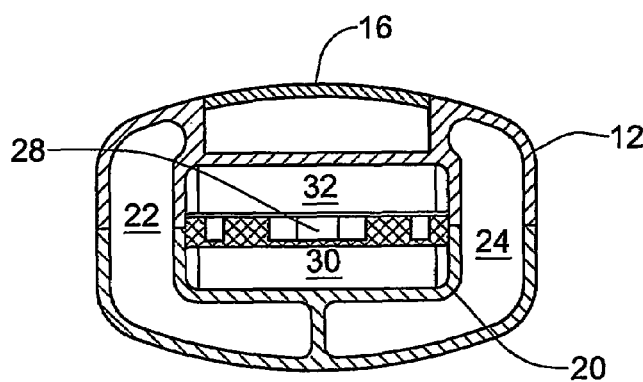
FIG. 3 is a transverse sectional view of the spirometer in FIG. 1.

With reference to FIGS. 1, 2 and 3, a jet spirometer 10 in accordance with one embodiment of the present invention comprises housing 12 with battery compartment 13, inlet port (mouthpiece) 14, mouthpiece cover 15, and battery cover 16. The housing 12 accommodates a measurement unit 20. Walls of the housing 12 and the measurement unit 20 define bypass flow path including channels 22 and 24. The bypass flow path is smooth, free of obstructions to the flow and is designed for minimal pressure drop. A measurement flow path passes through the measurement unit 20 starting at the measurement inlet 26.

Figure 4:
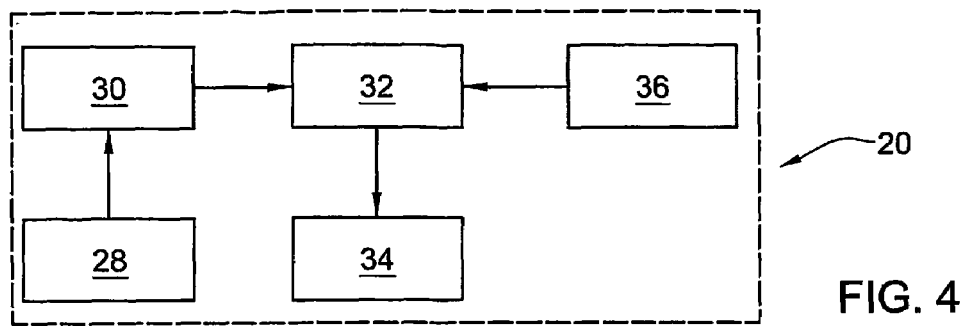
FIG. 4 is a functional flowchart of modules of the spirometer of FIG. 1.

With reference also to FIG. 4, the measurement unit 20 comprises a fluidic pulse generator (FPG) 28 known also as fluidic jet oscillator, pneumo-electric transducer 30, electronic processor 32, indicator block (display) 34, and power battery 36.

Figure 5:
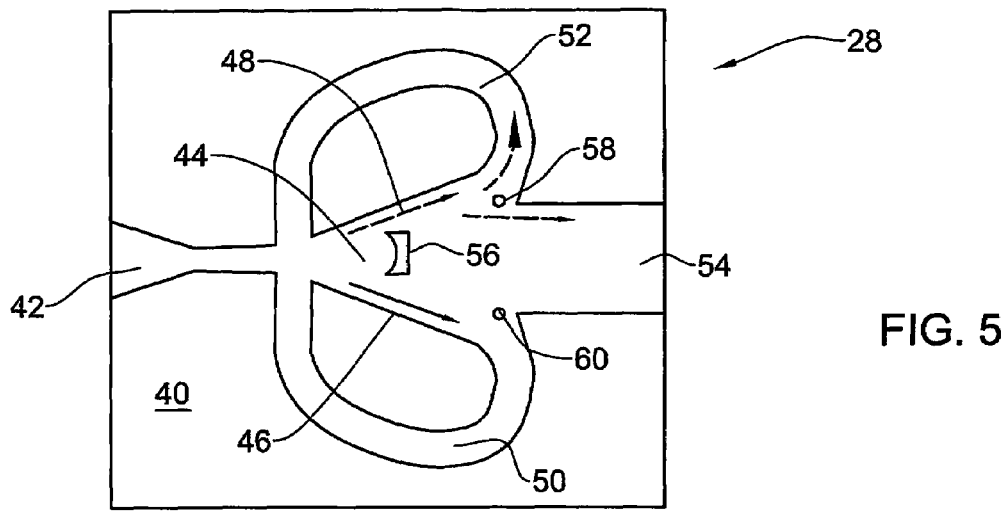
FIG. 5 is a schematic layout of the fluidic pulse generator (FPG) used in the spirometer of FIG. 1.

The fluidic pulse generator 28 is a bi-stable jet element with positive feedback. With reference to FIG. 5, the FPG 28 constitutes a flat plate 40 with cut-out channels of predetermined shape. These channels comprise: an inlet channel (nozzle) 42 connected to a diffuser 44 defined between two diverging walls 46 and 48; feedback channels 50 and 52 connecting downstream ends of the walls 46 and 48 to the diffuser inlet; and a wide outlet channel 54 opposite the diffuser outlet In the middle of the diffuser stands a flow divider 56, while two pressure pick-up ports 58 and 60 are disposed in the diffuser at the entrance of the feedback channels 50 and 52 respectively. The channels of the FPG may be designed such that the flow through the FPG—the measurement flow—is at least by an order of magnitude less than the bypass flow.

Figure 6:
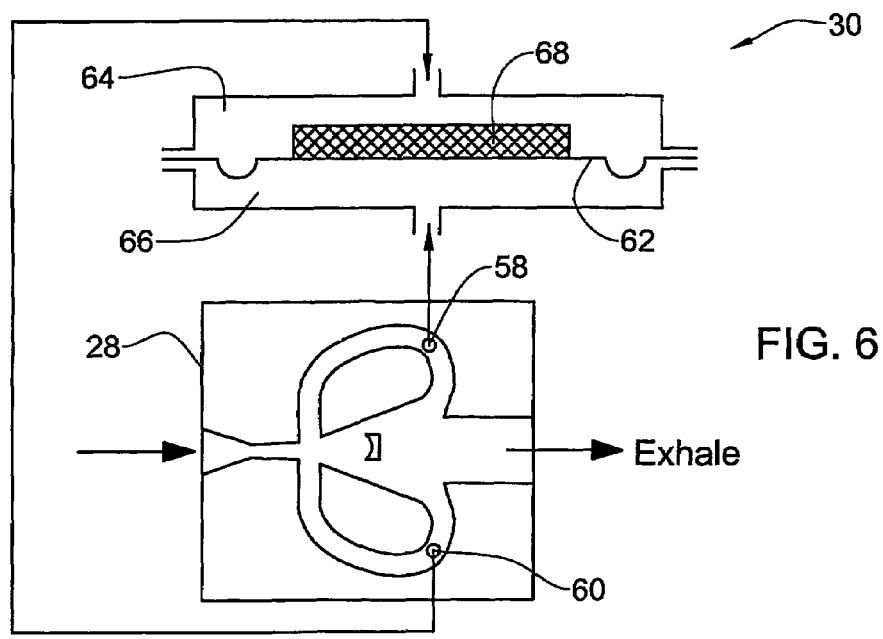
FIG. 6 is a scheme of pneumatic connections between the FPG of FIG. 5 and a differential pressure transducer.

With reference to FIG. 6, the pneumo-electric transducer 30 has a cavity with a membrane 62 dividing it into an upper chamber 64 and a lower chamber 66. The two chambers are in fluid communication with the pressure pick-up ports 58 and 60 of the FPG 28. A piezoelement 68 is fixed on the membrane and is adapted to convert the pressure differential across the membrane into electric output signal. The output signal line of the transducer 30 is connected to the input of the electronic processor 32 where the electric signal from the transducer is conditioned and processed.

The output of the electronic processor 32 is connected to the input of the indicator block 34 where the measured airflow rate and/or volume is presented by a suitable indication—as a color, number, geometrical, or another code.

In operation when conducting a test on the respiratory function of a patient, the exhaled air enters the inlet port 14 of the housing 12 and the airflow passes through the bypass channels 22, 24. A small portion of the airflow—measurement flow—enters the fluidic pulse generator 28 through the measurement inlet 26. The measurement airflow enters the inlet nozzle 42 and then the diffuser 44. In accordance with the Coanda effect, the air jet in the diffuser 44 sticks with one of the walls, for example 46, and proceeds towards the outlet channel 54. Part of the jet enters the feedback channel 50 and returns back to the inlet of the diffuser 44. This part of the jet disturbs (turbulizes) the boundary layer on the wall 46. As a result, the air jet is detached from the wall 46 and jumps to the opposite wall 48. Now a part of the jet enters the opposite feedback channel 52 and the cycle is repeated. The frequency of these jet swaps is roughly proportional to the flow rate through the FPG.

The pressure differential between the pick-up ports 58 and 60, which oscillates with the same frequency, is converted into oscillating electric signal by the piezoelement 68 in the pneumo-electric transducer 30. The oscillating signal is then fed to the electronic processor 32 for calculation of the flow rate and the total flow volume for a given time. The obtained data are sent to the indicator block 34 for display to the user.

A quantitative measure of the airflow rate and/or the volume of air passing through the spirometer is obtained in the electronic processor 32. Assuming that the relationship between the measured frequency generated in the FPG and the total flow rate through the spirometer is linear, a "pulse weight" coefficient Pw may be obtained by calibration of the spirometer. Methods of flow meters calibration per se are known in the art of aerodynamics. The Pw coefficient determines the volume of air passing through the spirometer as a whole (bypass channels and the FPG) per one pulse of the generated frequency. Thus, by counting the number of pulses, the whole volume of air passing through the spirometer for a predetermined time may be calculated, as well as the volume passing for a unit of time (flow rate).

Alternatively, if the above relationship is not assumed linear, then the Pw coefficient will be a function of the frequency. The non-linear relationship may be described by more coefficients obtained by calibration and stored in the electronic processor 32. Methods of non-linear calibration are also known per se.

Generally speaking, the proportion between the rate of the measurement flow passing through the FPG and the bypass flow rate is also dependent on the total flow rate. In the area of industrial/utility gas flow meters, attempts to keep this proportion constant have been made by dividing the bypass channel into a plurality of narrow channels, each with pressure drop equal to the pressure drop of the FPG However, this leads to a high total pressure drop which is not desirable in spirometry.

The spirometer may further include storage (memory) for measurement data and a communication device such as IR port or radio-frequency device (for example BlueTooth) for data exchange with an external device such as personal computer, preferably bi-directionally. Thus the measurement data mat be transferred over the internet and used in telemedicine. The communication device may include interface (wired or wireless) to a cellular phone enabling transmission of the data through the cellular phone network. Moreover, the miniature size of the spirometer allows its housing to be designed for mounting to the housing of a cellular phone. Alternatively, the spirometer and the cellular phone may be accommodated in an integral housing. Such combined device may share common microprocessor, software and display.

Figure 7:
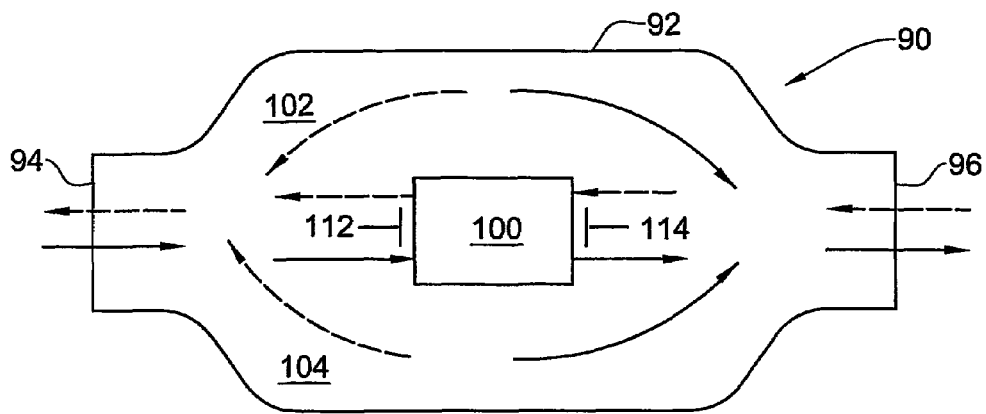
FIG. 7 is a schematic layout of an example of a spirometer in accordance with another aspect of the present invention.
Figure 8:
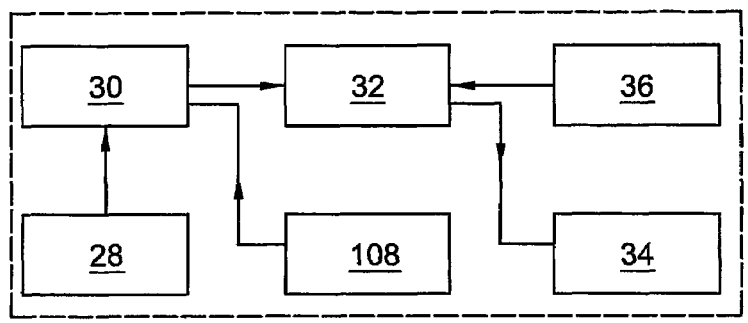
FIG. 8 is a functional flowchart of the spirometer in FIG. 7.
Figure 9:
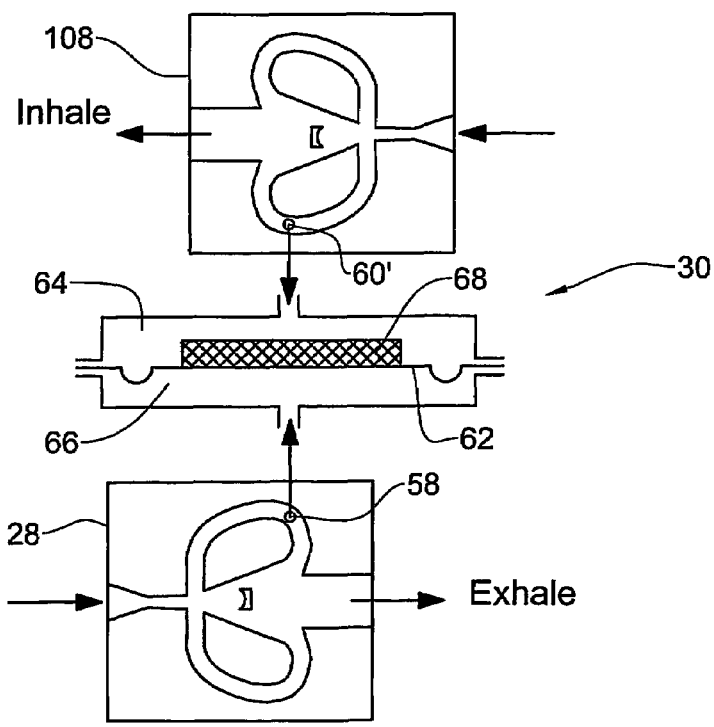
FIG. 9 is a scheme of pneumatic connections between two FPGs of the spirometer in FIG. 7 and a differential pressure transducer.

According to another embodiment of the present invention shown in FIGS. 7, 8 and 9, a jet spirometer 90 is designed for measuring flow rate and volume both at exhale and inhale. The jet spirometer 90 comprises housing 92 having an inlet port 94 and an outlet port 96 for the air flow.

A measurement unit 100 is disposed in the housing 92 and a bypass flow path including channels 102 and 104 is defined between the measurement unit and the housing. The bypass flow path is designed for minimal pressure loss both at exhale and at inhale.

With reference to FIG. 8, the measurement unit 100 comprises two fluidic pulse generators 28, 108 connectable to the flow via check valves 112, 114, pneumo-electric transducer 30, electronic processor 32, indicator block 34 and power battery 36.

The inlet and outlet channels of the two FPGs 28, 108 are located opposite the ports 94 and 96 of the housing, in mutually opposing directions. Each FPG has a check valve connected to it, such that FPG 28 with check valve 112 operates during exhale, while the FPG 108 with check valve 114 operates during inhale.

As shown in FIG. 9, in this case each of the two chambers of the pneumo-electric transducer 30 is in fluid communication with one pressure pick-up port of one FPG, port 60' of the FPG 108, and port 58 of the FPG 28, respectively. Thus the pressure pulses from the FPGs may be counted by one transducer both at inhaling and exhaling.

A scheme where each FPG has its own transducer, may work without check valves 112, 114, the inlet and outlet channels of both FPGs being always open. When, for example, the user exhales, the FPG 28 operates in its normal mode (straight flow) generating regular pressure pulses. The FPG 108 will also operate but in reverse flow, creating noise instead of regular pressure pulses. Similarly, if the user inhales, the FPG 108 will operate in its normal mode, while the FPG 28 will create noise. The front edge of the first regular pulse always comes before the noise—thus the processor 32 can always identify which of the FPGs is working in normal mode, i.e. whether the user is inhaling or exhaling. Accordingly, the processor will select the identified FPG for further measurement, until the flow through the spirometer keeps its direction.

Figure 10:
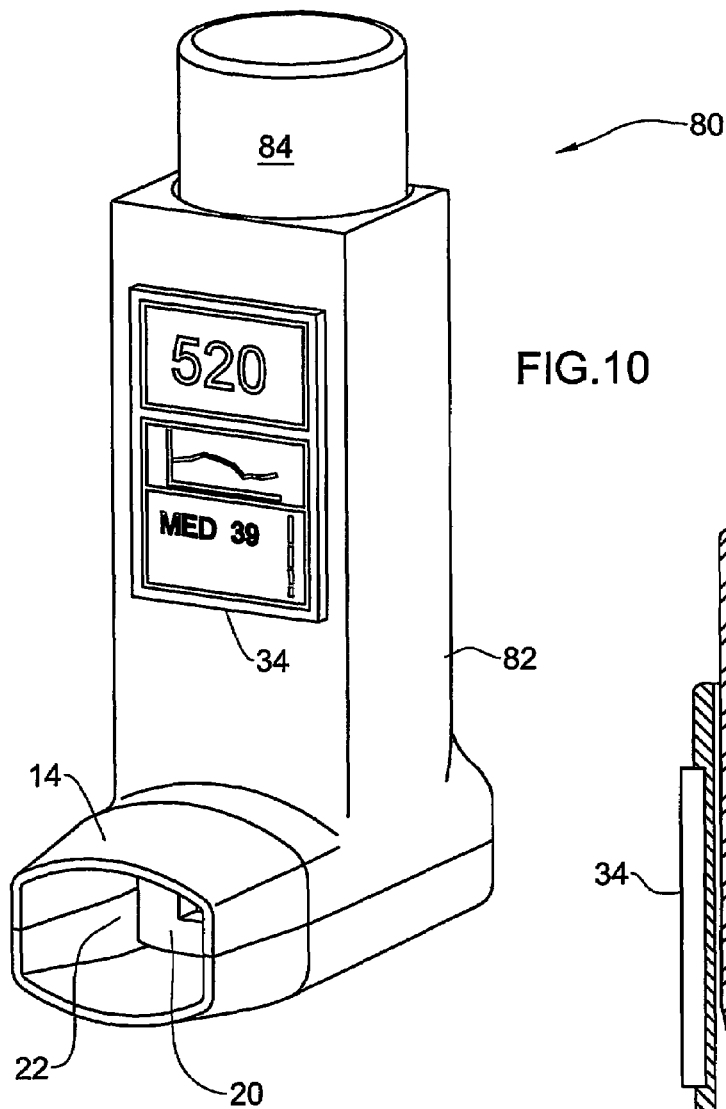
FIG. 10 is a perspective view of an example of a spirometer combined with a medicine dosage dispenser, in accordance with a further aspect of the present invention.
Figure 11:
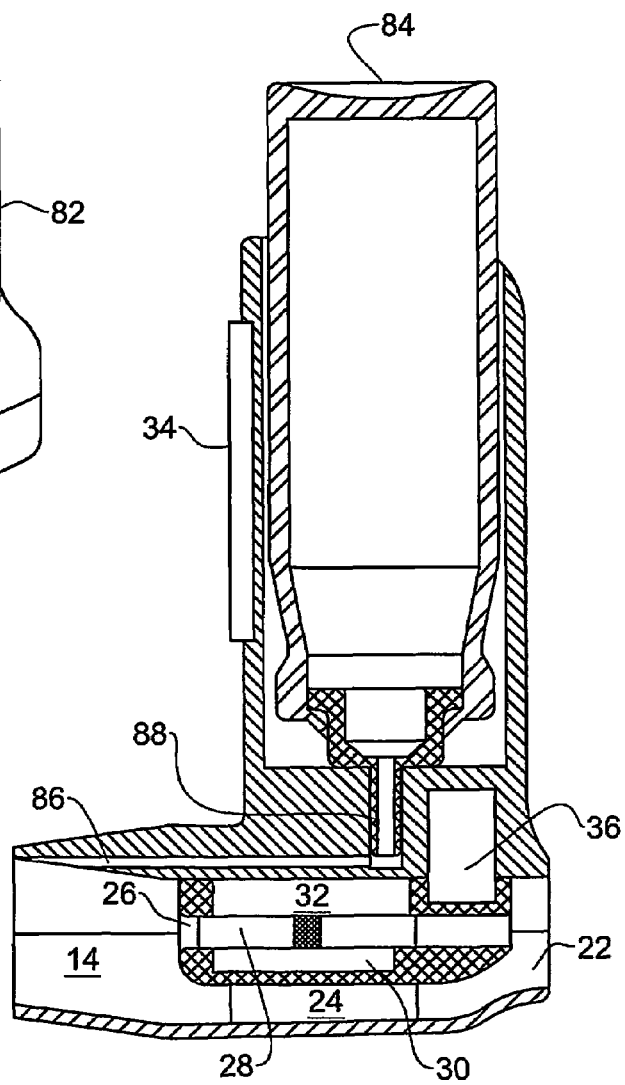
FIG. 11 is a sectional view of the combined spirometer of FIG. 10.

According to another embodiment of the present invention, the jet spirometer may include a medicine dosage dispenser. With reference to FIGS. 10 and 11, there is shown a combined spirometer-dispenser 80 having a housing 82. The spirometer part of the combined device 80 is similar to the above-described spirometer 10 and comprises inlet port (mouthpiece) 14, battery compartment 13, measurement unit 20 with measurement inlet 26, bypass channels 22 and 24. The measurement unit 20 comprises an FPG 28, pneumo-electric transducer 30, electronic processor 32, display 34, and power battery 36. The housing 82 further comprises a recess for accommodating a standard medicine (aerosol) container 84, and a delivery channel 86 connecting the dispensing nozzle 88 of the container 84 to the mouthpiece 14.

After making a measurement and reading the display 34, the patient may immediately and conveniently inhale the necessary dosage of medicine.

Figure 13:
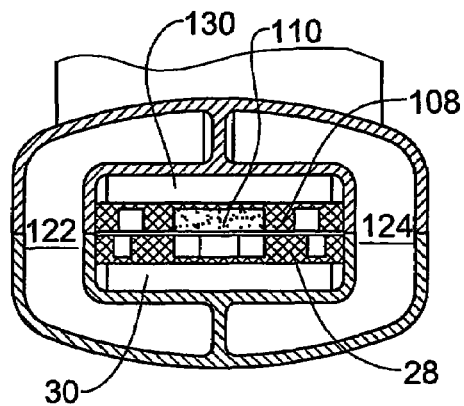
FIG. 13 is a transverse sectional view of the spirometer of FIG. 12.
Figure 12:
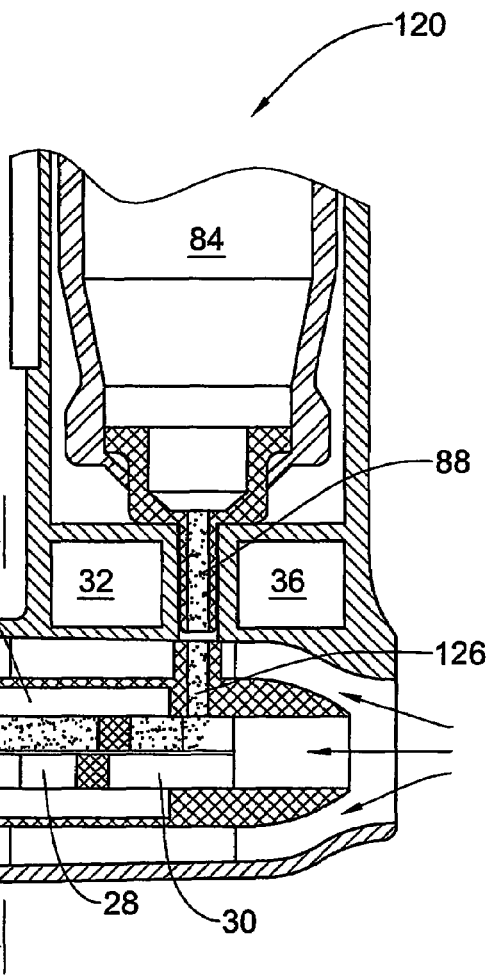
FIG. 12 is a sectional view of another example of a spirometer combined with a medicine dosage dispenser.
Figure 14:
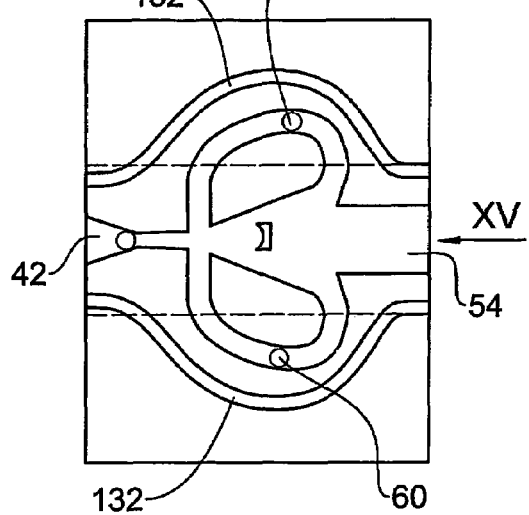
FIG. 14 is a plan view of an FPG with a surrounding bypass which may be used as a spirometer in accordance with a further aspect of the invention.
Figure 15:
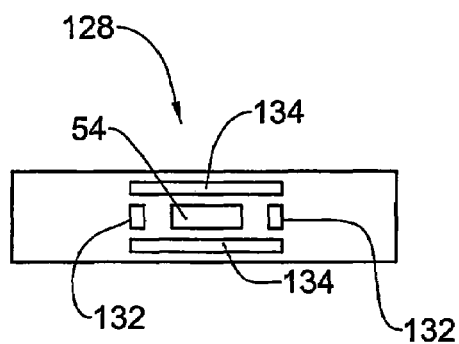
FIG. 15 is a front view of the FPG of FIG. 14.
Figure 16:
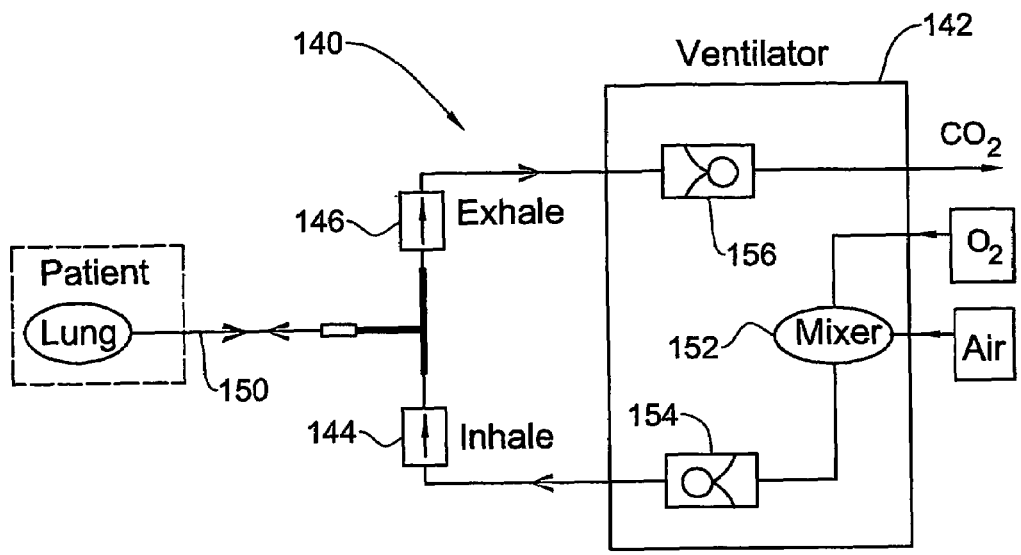
FIGS. 16 and 17 show schemes of a lung ventilation system using spirometers of the present invention.
Figure 17:
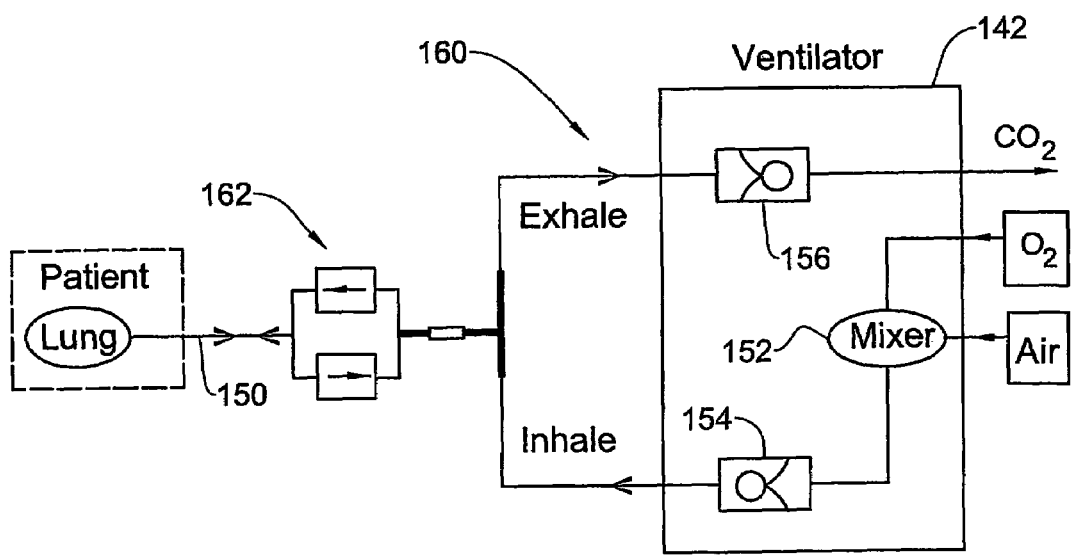

FIGS. 12 and 13 show an embodiment 120 of the spirometer-dispenser comprising a second, inverted FPG 108, accommodating the inhale flow. A delivery channel 126 in this embodiment delivers the aerosol medicine to the inlet nozzle of the second FPG. The flow pulses generated therein contribute to dispersing of the medicine and its better mixing with the airflow. Such FPG may be used just as a mixer for a medicine dispenser, without being a measurement device.

As seen in FIGS. 12 and 13, the bypass channel may be formed as an annular channel 122-124, surrounding the jet flow 110 exiting from the mixing FPG 108. Thus, the medicine-laden jet 110 remains in the core of the flow, isolated from the walls of the spirometer (inhaler) and from the user's throat. The medicine may be delivered deep into the trachea, without sticking to the mucous walls of the respiratory tract. The proportion of medicine reaching the bronchi and the alveoli will be larger and the overall dosage may be reduced.

An alternative structure is shown in FIGS. 14 and 15. In an FPG 128, a surrounding bypass channel 132-134 may be formed in the body of the fluidic pulse generator.

The above two aerodynamic arrangements may be used in any kind of dispenser, with or without measurement functions.

The spirometer of the present invention may be used as a constituent part of larger mobile or stationary measurement schemes as, for example, shown in FIGS. 16 and 17.

FIG. 16 shows a scheme of lung ventilation 140 comprising an artificial ventilation system 142, flowmeters 144 and 146, a T-connector 148 and an endotracheal tube 150 communicating with the patient's lungs. The ventilation system 142 comprises a mixer 152 and check valves 154 and 156.

As flowmeters 144 and 146, the spirometers of the present invention may be used, for example, the spirometer 10 of FIG. 2. It would be appreciated that the inlet and the outlet of the spirometer 10 should be suitably formed for connecting to the T-connector and the other piping in the system.

FIG. 17 shows a variation 160 of the lung ventilation scheme 140 in FIG. 16. Here, a single flowmeter 162 is used, which may be the spirometer 90 and its variations comprising two FPGs, described with reference to FIGS. 7, 8 and 9.

Although a description of specific embodiments has been presented, it is contemplated that various changes could be made without deviating from the scope of the present invention. For example, the present invention could be modified such that pulses of flow velocity could be counted instead of pressure pulses, by means of hot-wire anemometer or other means known per se in the art.

The invention claimed is:

1. A medical spirometer comprising a housing with a flow inlet and a flow outlet, and a measurement unit (MU), for measuring rate of total flow between said inlet and said outlet when a user exhales through said spirometer, said MU comprising a fluidic jet oscillator adapted to generate oscillating flow characterized by an oscillating parameter dependent on rate of flow through said jet oscillator, and a transducer adapted to convert said oscillating parameter into an oscillating electric signal, wherein said MU is disposed within said housing so as to form a bypass flow path defined between an outer surface of said MU and an inner surface of said housing, and a measurement flow path defined through said fluidic jet oscillator, such that said total flow is divided into a bypass flow and a measurement flow.

2. The spirometer of claim 1, wherein said bypass flow path is free of obstructions increasing its pressure drop.

3. The spirometer of claim 1, wherein measurement flow rate is at least an order of magnitude less than bypass flow rate.

4. The spirometer of claim 1, wherein said spirometer is of pocket size.

5. The spirometer of claim 1, wherein the frequency of said oscillating parameter is dependent on the rate of flow through said jet oscillator and said MU further comprises an electronic circuit adapted to measure said frequency and to derive said total flow rate therefrom.

6. The spirometer of claim 5, wherein said electronic circuit is adapted to store coefficients obtained in previous calibration of said spirometer and to use them for deriving said total flow rate from said frequency.

7. The spirometer of claim 5, wherein said electronic circuit is adapted to measure said frequency by counting pulses of said oscillating parameter.

8. The spirometer of claim 7, wherein said electronic circuit is further adapted to integrate said total flow rate, thereby measuring total flow volume per predetermined time.

9. The spirometer of claim 1, wherein said oscillating parameter is flow velocity.

10. The spirometer of claim 9, wherein said transducer is hot wire.

11. The spirometer of claim 1, wherein said oscillating parameter is flow pressure.

12. The spirometer of claim 11, wherein said transducer is pressure transducer.

13. The spirometer of claim 12, wherein said pressure transducer is of differential type, said jet oscillator has two feed-back channels, each with a pressure port, and one of said pressure ports is connected to one side of the pressure transducer, while the other one of said pressure ports is connected to the other side of the pressure transducer.

14. The spirometer of claim 12, wherein said pressure transducer comprises a flexible membrane and a piezoelectric element mounted thereon.

15. The spirometer of claim 1, wherein said measurement flow path is a first measurement flow path, and said MU comprises a second fluidic jet oscillator adapted to generate oscillating flow dependent on rate of flow therethrough and defining a second measurement flow path within said MU, parallel and opposite to the first measurement flow path, such that a second measurement flow is created when the user inhales through said spirometer.

16. The spirometer of claim 15, further comprising valve means such that the first measurement flow path is open only when the user exhales while the second measurement flow path is open only when the user inhales.

17. The spirometer of claim 16, wherein said valve means include one check valve associated with the first measurement flow path and one check valve associated with the second measurement flow path.

18. The spirometer of claim 15, wherein said oscillating parameter is flow pressure, said transducer is pressure transducer, and both jet oscillators are connected to said transducer.

19. The spirometer of claim 15, wherein said MU further comprises a second transducer adapted to convert an oscillating flow parameter of the second jet oscillator into a second oscillating electric signal, such that at exhaling the first jet oscillator works in straight flow while the second jet oscillator works in reverse flow and vice-versa, the two transducers producing oscillating electric signals with different patterns associated with said straight flow and said reverse flow, and the spirometer includes an electronic processor adapted to recognize whether the user inhales or exhales by said different patterns.

20. The spirometer of claim 19, wherein said patterns differ in that the oscillating signal associated with the reverse flow is noise while the oscillating signal associated with the straight flow has regular pulse structure with the front edge of the first pulse coming before said noise.

21. The spirometer of claim 1, comprising valve means such that a measurement flow through said jet oscillator is created also when the user inhales through said spirometer, thereby enabling measuring of total flow rate at inhale.

22. The spirometer of claim 1, wherein at least one of said jet oscillator and said MU can assume a second position with respect to said housing, such that a measurement flow through said jet oscillator would be created when the user inhales through said spirometer, thereby enabling measuring of total flow rate at inhale.

23. The spirometer of claim 1, further comprising a means to display flow measurement results to the user.

24. The spirometer of claim 23, further comprising means for identifying a medical condition using said flow measurement results, and for warning the user.

25. The spirometer of claim 24, further comprising input means for entering personal data of the user, said means for identifying a medical condition being adapted to use said personal data.

26. The spirometer of claim 24, further comprising means for suggesting preventive measures to the user upon identifying said medical condition.

27. The spirometer of claim 1, further comprising means for storing measurement data.

28. The spirometer of claim 27, further comprising communication means for transmitting said data to an external device.

29. The spirometer of claim 28, wherein said communication means allow for bidirectional data exchange with said external device.

30. The spirometer of claim 28, wherein said communication means include interface to a cellular phone enabling transmission of said data through cellular phone network.

31. The spirometer of claim 30, wherein said housing is designed for mounting to the housing of said cellular phone.

32. The spirometer of claim 30, further including program means transferable to or resident in said cellular phone allowing to display flow measurement results on a display of said cellular phone.

33. The spirometer of claim 28, wherein said communication means include a built-in cellular phone enabling transmission of said data through a cellular phone network.

34. The spirometer of claim 1, wherein said housing is adapted to accommodate a dispenser with medicine for inhaling.

35. The spirometer of claim 34, wherein said housing has a delivery channel for delivery of said medicine for inhaling to the user's mouth.

36. The spirometer of claim 35, wherein said delivery channel connects an outlet of said dispenser to said bypass channel.

37. The spirometer of claim 35, wherein an outlet end of said delivery channel is disposed such that said medicine is delivered to a central core of inhaled air flow.

38. The spirometer of claim 35, further comprising a second fluidic jet oscillator defining a second flow path such that a second oscillating flow is created when the user inhales through said spirometer, said delivery channel connecting an outlet of said dispenser to the inlet of the second jet oscillator, such that the medicine passes through said second flow path.

39. The spirometer of claim 38, wherein a bypass channel is formed in said second fluidic jet oscillator as an annular channel surrounding said second flow path.

40. A medical spirometer comprising a housing with a flow inlet and a flow outlet, and a measurement unit (MU) disposed in said housing, for measuring rate of total flow between said inlet and said outlet when a user exhales or inhales through said spirometer, said MU comprising a first and a second fluidic jet oscillators each having an inlet and an outlet defining straight flow direction used for measurement and an inoperative, reverse flow direction, and being adapted to generate oscillating flow characterized by an oscillating parameter dependent on rate of straight flow through the jet oscillator, and respective first and second transducers adapted to convert the oscillating parameter into an oscillating electric signal, wherein the fluidic jet oscillators are in fluid communication with said inlet and said outlet, such that when the user exhales, the first jet oscillator works in the straight flow while the second jet oscillator works in the reverse flow and vice-versa, the two transducers producing oscillating electric signals with different patterns associated with said straight flow and said reverse flow, and the spirometer further includes an electronic processor adapted to recognize whether the user inhales or exhales by said different patterns.

41. The spirometer of claim 40, wherein said patterns differ in that the oscillating signal associated with the reverse flow is noise while the oscillating signal associated with the straight flow has regular pulse structure with the front edge of the first pulse coming before said noise.

42. An inhaler-dispenser device comprising a housing adapted to accommodate a dispenser with medicine for inhaling, said housing having an inhaling passage with inlet air opening and outlet mouthpiece such that, upon inhaling, an airflow runs from said inlet to said outlet, the housing further having a delivery channel for delivery of said medicine into said airflow, wherein an outlet end of said delivery channel is such disposed relative to the inhaling passage that, at inhale, a dose of said medicine is delivered to a central core of said airflow in the passage.

43. An inhaler-dispenser device comprising a housing adapted to accommodate a dispenser with medicine for inhaling, said housing further having an inhaling passage with inlet air opening and outlet mouthpiece such that, upon inhaling, an airflow runs from said inlet to said outlet, the housing further having a delivery channel for delivery of said medicine into said airflow, wherein said inhaling passage includes a fluidic jet oscillator with an inlet in fluid communication with said inlet opening and an outlet in fluid communication with said mouthpiece, said delivery channel opening into the inlet of said fluidic jet oscillator.

44. The inhaler-dispenser device of claim 43, wherein said inhaling passage further comprises an annular bypass channel in fluid communication with said inlet opening and said mouthpiece, said bypass channel surrounding said fluidic jet oscillator such that upon inhaling, an outlet flow of said fluidic jet oscillator carrying said medicine is surrounded by a flow through said bypass channel.

45. The inhaler-dispenser device of claim 43, wherein said fluidic jet oscillator comprises an annular bypass channel in fluid communication with said inlet opening and said mouthpiece, said bypass channel surrounding the outlet of said fluidic jet oscillator such that upon inhaling, an outlet flow of said fluidic jet oscillator carrying said medicine is surrounded by a flow through said bypass channel.

46. A method for measurement of a user's inhale and exhale rate of flow by means of two fluidic jet oscillators, each having an inlet and an outlet defining straight flow direction used for measurement and an inoperative, reverse flow, and adapted to generate oscillating flow characterized by an oscillating parameter dependent on rate of the straight flow through the jet oscillator, and two respective transducers adapted to convert said oscillating parameter into an oscillating electric signal, said method comprising:

arranging the fluidic jet oscillators in parallel and opposite directions, both being open to inhale and exhale flow, such that when the user exhales, the first jet oscillator works in the straight flow and when the user inhaled, the second jet oscillator works in the straight flow;

exhaling or inhaling providing flows through said fluidic jet oscillator;

obtaining two oscillator electric signal from said two transducers and processing them to identify which of the signals is associated with said straight flow using pattern difference between the straight flow and the reverse flows signals, and from which transducer this signal comes, and determining the flow rate from rate from the identified signal.

47. The method of claim 43, wherein said reverse flow oscillating signal is noise while said straight flow oscillating signal has regular pulse structure with the front edge of the first pulse coming before said noise.

* * * * *